US011109784B2

(12) United States Patent
Adalian et al.

(10) Patent No.: US 11,109,784 B2
(45) Date of Patent: Sep. 7, 2021

(54) METAL-ENZYME SANDWICH LAYERS

(71) Applicant: CALIFORNIA INSTITUTE OF TECHNOLOGY, Pasadena, CA (US)

(72) Inventors: Dvin Adalian, Pasadena, CA (US); Samson Chen, Pasadena, CA (US); Muhammad M. Jilani, Pasadena, CA (US); Axel Scherer, Pasadena, CA (US); Xiomara Linnette Madero, Pasadena, CA (US); Richard Smith, Pasadena, CA (US)

(73) Assignee: CALIFORNIA INSTITUTE OF TECHNOLOGY, Pasadena, CA (US)

(*) Notice: Subject to any disclaimer, the term of this patent is extended or adjusted under 35 U.S.C. 154(b) by 321 days.

(21) Appl. No.: 16/191,357

(22) Filed: Nov. 14, 2018

(65) Prior Publication Data
US 2019/0307378 A1   Oct. 10, 2019

Related U.S. Application Data

(60) Provisional application No. 62/654,701, filed on Apr. 9, 2018.

(51) Int. Cl.
*A61B 5/1486* (2006.01)
*A61B 5/145* (2006.01)
*A61B 5/1473* (2006.01)

(52) U.S. Cl.
CPC ........ *A61B 5/14865* (2013.01); *A61B 5/1473* (2013.01); *A61B 5/14532* (2013.01); *A61B 5/14546* (2013.01)

(58) Field of Classification Search
None
See application file for complete search history.

(56) References Cited

U.S. PATENT DOCUMENTS

| | | | |
|---|---|---|---|
| 7,959,791 B2 | 6/2011 | Kjaer et al. | |
| 9,681,828 B2 | 6/2017 | Jacks et al. | |
| 2007/0227907 A1* | 10/2007 | Shah | C25D 5/10 205/777.5 |

FOREIGN PATENT DOCUMENTS

| | | | | |
|---|---|---|---|---|
| CN | 104761697 A | * | 7/2015 | ............ C08G 18/61 |
| CN | 105943058 A | | 9/2016 | |
| JP | 2000081409 A | | 3/2000 | |
| KR | 20140033668 A | | 3/2014 | |
| WO | 2019/209377 A2 | | 10/2019 | |

OTHER PUBLICATIONS

Venkataramani Anandan, Yeswanth L Rao, Guigen Zhang, Nanopillar array structures for enhancing biosensing performance, 2006, International journal of nanomedicine, pp. 73-39 (Year: 2006).*

(Continued)

*Primary Examiner* — Etsub D Berhanu
*Assistant Examiner* — Tyra Faith Bookhart
(74) *Attorney, Agent, or Firm* — Steinfl + Bruno, LLP

(57) ABSTRACT

Measurement of target analytes is carried out with an enzyme-based sensor. The enzyme hydrogel is protected by a porous layer of a metallic material. The size of the pores is small enough to prevent degradation of the enzyme layer caused by the immune system of an organism, but large enough to allow transfer of molecules that participate in the electrochemical reaction allowing the enzyme to detect the target analytes.

26 Claims, 11 Drawing Sheets

(56) References Cited

OTHER PUBLICATIONS

Marc Delvaux, Sophie Demoustier-Champagne, Immobilisation of glucose oxidase within metallic nanotubes arrays for application to enzyme biosensors, 2002, Biosensors and Bioelectronics, vol. 18, Issue 7, pp. 943-951 (Year: 2002).*
International Search Report and Written Opinion for International Application No. PCT/US2018/063486 filed Nov. 30, 2018 on behalf of California Institute of Technology. dated Dec. 4, 2019. 10 pages.

* cited by examiner

METAL-ENZYME SANDWICH LAYERS

CROSS REFERENCE TO RELATED APPLICATIONS

The present application claims priority to U.S. Provisional Patent Application No. 62/654,701, filed on Apr. 9, 2018, the disclosure of which is incorporated herein by reference in its entirety.

STATEMENT OF INTEREST

This invention was made with government support under Grant No. HR0011-15-2-0050 awarded by DARPA. The government has certain rights in the invention.

TECHNICAL FIELD

The present disclosure relates to biosensing. More particularly, it relates to metal-enzyme sandwich layers.

BRIEF DESCRIPTION OF DRAWINGS

The accompanying drawings, which are incorporated into and constitute a part of this specification, illustrate one or more embodiments of the present disclosure and, together with the description of example embodiments, serve to explain the principles and implementations of the disclosure.

SUMMARY

Figure 1:
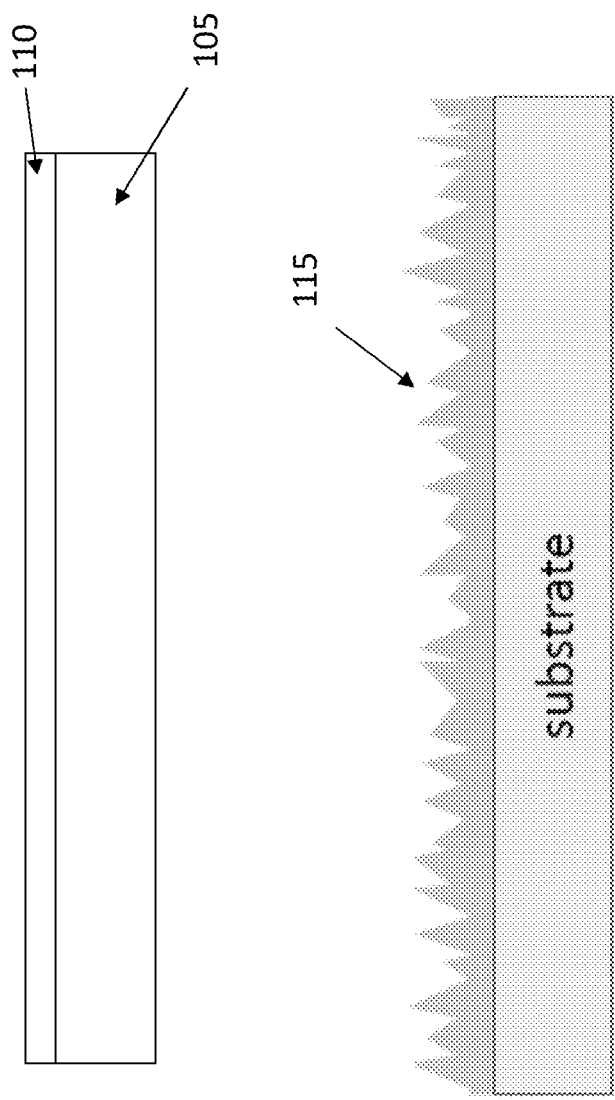
FIGS. 1-2 illustrate exemplary steps in the fabrication process of a sensor.

In a first aspect of the disclosure, a sensing device is described, the sensing device comprising: a working electrode on a substrate; wherein: the working electrode comprises: a metallic layer contacting the substrate; an enzyme layer on the metallic layer; and a metallic porous layer on the enzyme layer, and the working electrode, the metallic porous layer, and the enzyme layer are configured to detect a target analyte through an electrochemical reaction.

DETAILED DESCRIPTION

Layers containing enzyme molecules are important for the electrochemical measurement of glucose, lactate, and many other metabolites of medical importance in the body. As known to the person of ordinary skill in the art, an enzymatic reaction can be used to selectively convert analytes of interest into by-products, releasing electroactive compounds during chemical reactions involving the analyte molecules. Electrochemical measurement of the rate of electroactive compound production can then provide concentration data of the analyte molecules. These measurements are not generally error-free, since the enzyme reaction may not be fully selective to the material of interest. In other words, the enzyme reaction may occur with false positives. Another factor is that the reagents necessary for the reaction to occur should be present in sufficient quantity, otherwise the electrochemical measurement will be limited by the reagents' quantity and not be entirely accurate. Further, the conversion rate from the enzyme should be high enough to generate electroactive compounds proportional to the analyte molecules, otherwise the signal can be lost in the noise.

In some embodiments, the electroactive compounds may be ions. However, in some embodiments, the electroactive compounds may be molecules other than ions. For example, the product of interest in the typical glucose oxidase reaction (hydrogen peroxide) is not an ion. In the present disclosure, some embodiments may refer to ions as the electroactive compounds, however these embodiments may also be implemented more generally without ions but with non-charged electroactive compounds. In the present disclosure "electroactive compounds" refer to ions and non-charged compounds that are capable of generating currents through an electrode through chemical reactions on the surface of that electrode.

If a significant current from the electroactive product can be collected, accurate measurement of metabolic biomarkers is possible, as long as the enzyme molecules remain active. Therefore, enzyme degradation has to be taken into account, and prevented or at least reduced to prolong longevity of the sensor. The efficiency of conversion for the analyte reaction into measured current is characterized by the conversion efficiency, which can be optimized if electroactive products are effectively collected onto the measurement electrode and are not lost to the surrounding environment through diffusion. The reaction rate should also be limited by the presence of the analyte of interest, and the concentration gradient of reagents to the enzyme molecules maintained by an adequate turnover rate.

Enzyme reactions have been used since the 1960s to measure glucose and other analytes. The first electrochemical glucose detector measured the current on a working electrode, biased with a negative 0.6 V with respect to a counter electrode, in order to collect charge from hydrogen peroxide that is generated by an enzymatic reaction between glucose and oxygen, catalyzed by glucose oxidase (GOx). In this catalytic reaction, glucose is oxidized to hydrogen peroxide and D-glucono-lactone. The electronic current from the hydrogen peroxide conversion to water and oxygen at the metallic working electrode was measured with a potentiostat. The current is proportional to the glucose concentration over a wide range of concentrations. Since the early 1960s, many other enzymes, both oxidases and dehydrogenases, have been identified to measure other analytes of interest. Such enzymes can selectively react with glucose, lactate, alcohol, urea, cholesterol, xanthine, and several dozens of other analytes of interest.

In electrochemical enzyme-based sensors, the conversion efficiency of analyte molecules into measurable current generally changes over time, as enzyme molecules are attacked, dissolved or lose their co-factors. These processes lead to the deterioration of the sensitivity and accuracy of the sensor over time. There exist several failure modes for electrochemical sensors that rely on enzymatic reactions. For example, enzymes can deteriorate by becoming oxidized due to the molecular compounds in their surrounding environment, or due to the reactive compounds that the sensors themselves generate. Enzymes can also lose the co-factors which enable the efficient reaction with analytes. Other necessary reagents for the enzymatic reaction, such as oxygen for oxidase enzymes, can be depleted, or the reactive enzyme film can simply delaminate by degradation of its adhesion to the substrate. When sensors are located within living organisms, these failure modes are generally accelerated, as the organism's immune system will attack the sensor through its foreign body response, and contribute to enzyme deterioration by oxidation. In vivo implants can become encapsulated, a process through which the immune response builds scar tissue diffusion barriers around the implanted device, preventing reagents and analytes from penetrating to the sensor electrodes and isolating the implant from the rest of the organism. All of these effects ultimately limit the sensor lifetime, or the length of time during which the electrochemical sensor can provide useful and accurate information. Most sensors are limited to several weeks in the challenging environments encountered in living organisms.

The present disclosure describes new methods for avoiding the common degradation mechanisms and prolonging the lifetime of enzyme-based electrochemical sensors, and other sensors that rely on monitoring selective (binding) reactions on or close to electrochemically-active contacts. Typically, electrodes are used to form electrochemical sensors by either using needle or wire geometries or by defining electrodes on flat surfaces. Ideally, electrode materials should be inert to the surrounding and not suffer from rapid corrosion. Platinum, gold, tungsten, iridium and titanium are therefore preferred materials since these are bio-compatible materials that do not deteriorate rapidly in the body, and do not generate deleterious immune system responses.

The impedance of these electrodes ultimately determines the current that can flow through the electrodes at a given voltage, as it is desirable for electrodes to minimize that circuit resistance in order to maximize the sensor sensitivity and the signal to noise ratio. This impedance can be modified by changing the surface area of the electrode. An increased surface area can be accomplished by increasing the lateral dimensions of the sensor, or by fabricating a three-dimensional electrode surface with an increased surface area for the same lateral dimensions. For example, the surface area can be increased through corrugation, by growing sponge-like geometries, or by fabricating regular or irregular nano-pillars or jagged structures. Typically, large surface-to-volume ratio electrodes can provide low impedance contacts to electrochemical reactions.

In traditional electrochemical sensors that rely on monitoring the ion generation of enzymatic reactions, the metal contact surface is coated with a thin adhesive layer that contains the enzyme. This layer is often called a "hydrogel", as it consists of a relatively porous material that enables the smaller molecule analytes (glucose, lactate, etc.) to diffuse through the layer to react with enzyme molecules that are immobilized within the molecular structure of this layer. A traditional chemistry used in glucose monitors is the glutaraldehyde system, a polymer that cross-links to form a chemically stable scaffold into which enzyme molecules can be immobilized. The polymer is porous enough to enable the enzyme molecules to remain active, and enable reagents to enter and products to leave the polymer. In commercial sensors, the glutaraldehyde-based layer containing the enzyme is typically several micrometers thick. The enzyme molecules generate ions that need to travel through this thickness of several micrometers, in order to be read at the electrode's surface. Unfortunately, any residual glutaraldehyde is immunogenic and can accelerate the natural immune response. Therefore, the glutaraldehyde-based layer is generally covered with a protection layer consisting of polyurethane or PEGylated with polyethylene glycol to reduce the immune response. These additional layers often reduce the sensitivity of the enzyme sensor, and are slowly eroded as they are attacked by natural oxidizing species, in turn leading to relatively short sensor lifetimes.

The present disclosure describes a method for prolonging the lifetime of enzyme-based electrochemical sensors. The approach uses a thin metal layer deposited on the top surface of a thin layer containing the active enzyme. For example, platinum can be deposited in a very porous geometry often referred to as "platinum black". Other materials such as titanium, gold or tungsten can also be used for fabricating a metallic porous layer that allows target analytes, reagents and by-products to move through the porous electrode in both directions, thus allowing access to the enzyme hydrogel underneath. The platinum (or other metal) layers can be deposited through a vacuum deposition process in which platinum is sputtered from a platinum target and deposited onto the sample. The sputter deposition process enables the control of both the thickness and the microstructure of the platinum layer by adjusting the deposition parameters, which include the voltage, power, and vacuum pressure during the deposition. Therefore, a platinum black layer can be used as a low-impedance contact surface for electrochemical electrodes. Sputter deposition is not the only way to deposit metals, and alternative methods include evaporation from a heated source. The source can be heated through electrical resistance methods, or with an electron beam. In other embodiments, other methods of deposition can be used, such as pulsed laser deposition. The key requirement of the deposition technique is that the local heating of the enzyme layer and the time required for the deposition should be minimized. Local heating could, in fact, degrade the enzyme layer. Although corrosive solutions may be needed for deposition of materials, it is also possible to deposit metal layers by electroplating or electroless plating from plating baths.

Instead of depositing a single enzyme-containing active layer on top of the platinum electrode layer, the present disclosure describes the deposition of a platinum/enzyme/platinum sandwich or multilayer. The structure comprises a top platinum layer which is relatively porous to enable analytes to reach the enzyme molecules in the middle layer, and a bottom platinum layer which acts as an electrode. This approach brings with it several important advantages. The platinum layer protects the enzyme layer underneath from oxidizing species that would attack the polymer through the immune response process. The pores in the top metallic layer are nanoscale, therefore the porous platinum layer prevents the immune system from probing and recognizing the underlying chemistry, removing the immunogenic behavior. In fact, the active components of the immune system are generally larger than a nanoscale pore. The top platinum layer optionally acts as another contact surface that captures escaping ions that would otherwise be lost, and enables their contribution to the electrical measurement. This is possible if the top platinum layer is electrically connected to the bottom platinum layer, either through vias through the enzyme layer or with electrical pathways around the enzyme layer. The platinum layer also enables the retention of oxygen, which is generated when peroxide ions react at the metal surface converting into water and dissolved oxygen. The oxygen is needed for subsequent reactions that require oxygen as a reagent, for the enzyme assisted conversion to successfully take place. The distance between the bottom platinum layer and the top platinum layer can be reduced to control the loss of co-factor through diffusion to the solution surrounding the sensor. All of these effects have been shown to improve the linearity of the glucose response of the sensor.

Figure 9:
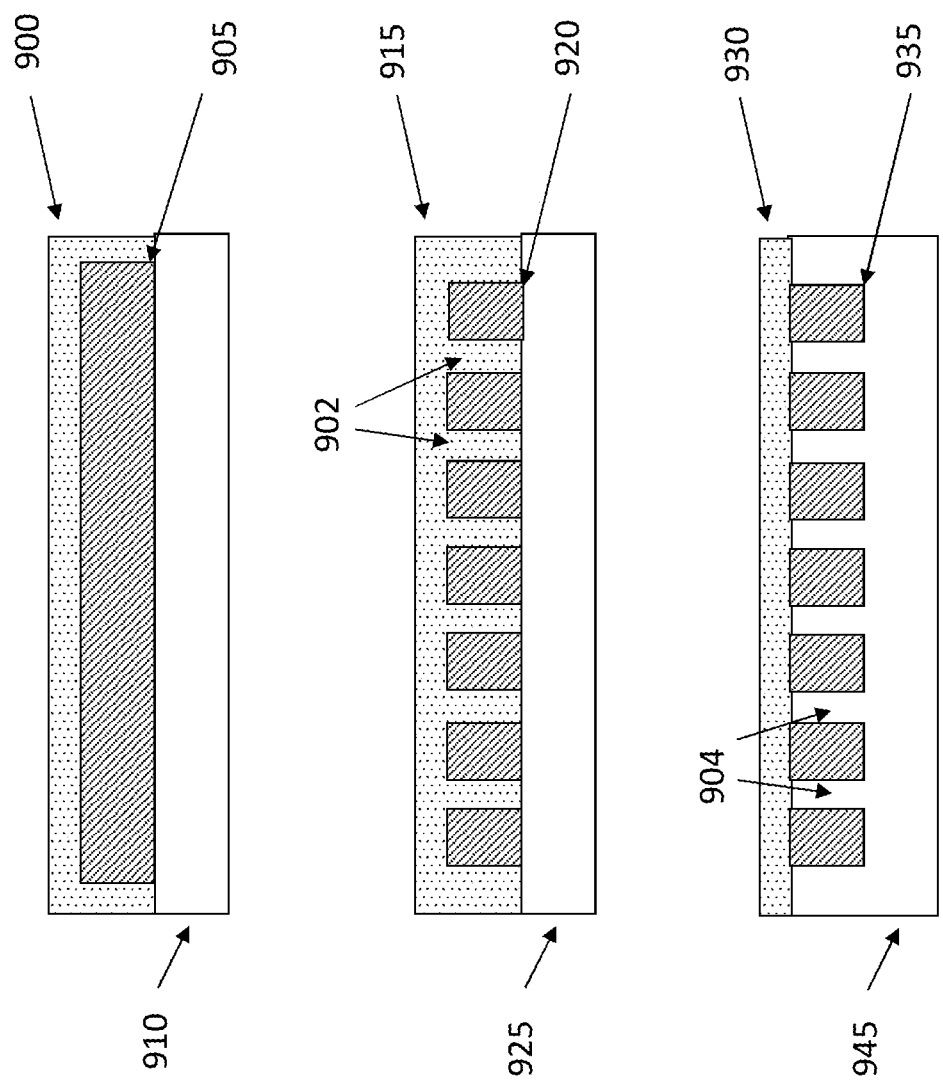
FIGS. 9-10 illustrate different embodiments of sensing devices.

In some situations, it may be preferable to electrically attach the top porous metal layer to the bottom electrode. This process can effectively double the available electrode area, which may be desirable in cases where sensitivity is important. The attachment can be carried out in several ways. As shown in the cross-sections of FIG. 9, the enzyme-based sensing layer (905) may be fabricated to be slightly smaller than the bottom electrode layer (910). In other words, the lateral dimensions of the enzyme layer are slightly smaller, leaving some space at the sides. The top conductive porous layer (900) may then be fabricated to be larger than the enzyme-based sensing layer. In this way, the top layer is electrically connected to the bottom electrode layer with conductive pathways around the periphery of the enzyme layer. Alternatively, the enzyme-based sensing layer (920) may be fabricated with multiple holes or vias (902), through which the top porous layer (915) is electrically connected to the bottom electrode layer (925). These holes may be formed by lithographic patterning techniques, and in some cases these holes may be formed by adjusting the deposition parameters of the enzyme-based sensing layer so that it natively contains holes. One advantage of this fabrication technique is that the large number of conductive attachment points improves both the reliability of the electrical connection and its mechanical reliability. Another way of forming these conductive attachments is to fabricate the bottom electrode layer (945) so that it has pillars (904). The enzyme-based sensing layer (935) may then be deposited onto the bottom electrode layer (945), leaving the top surface of the pillars exposed. When the porous layer (930) is deposited onto the structure, it contacts the top surfaces of the pillars, forming a multitude of conductive pathways between the top and bottom electrodes.

These conductive attachments can themselves increase the effective electrode area, as each conductive attachment adds some surface area. Thus, in scenarios where an increased electrode area is beneficial, the width of each conductive attachment may be as small as 5-40 nanometers, which is the limit of most practical fabrication techniques for this type of structure. The spacing between attachments may be as small as 100 nanometers. However, such attachments may be fragile and are generally complex to produce. If such high effective surface area is unnecessary or potentially not beneficial due to higher background currents, larger attachments, such as 1 to 25 micrometers, and a larger spacing, such as 1 to 25 micrometers, are preferable. The shapes of these attachments are typically dictated by the fabrication technique, and could have, for example, circular or rectangular cross sections. The height of these attachments is generally selected based on the desired thickness of the enzyme sensing layer.

Figure 10:
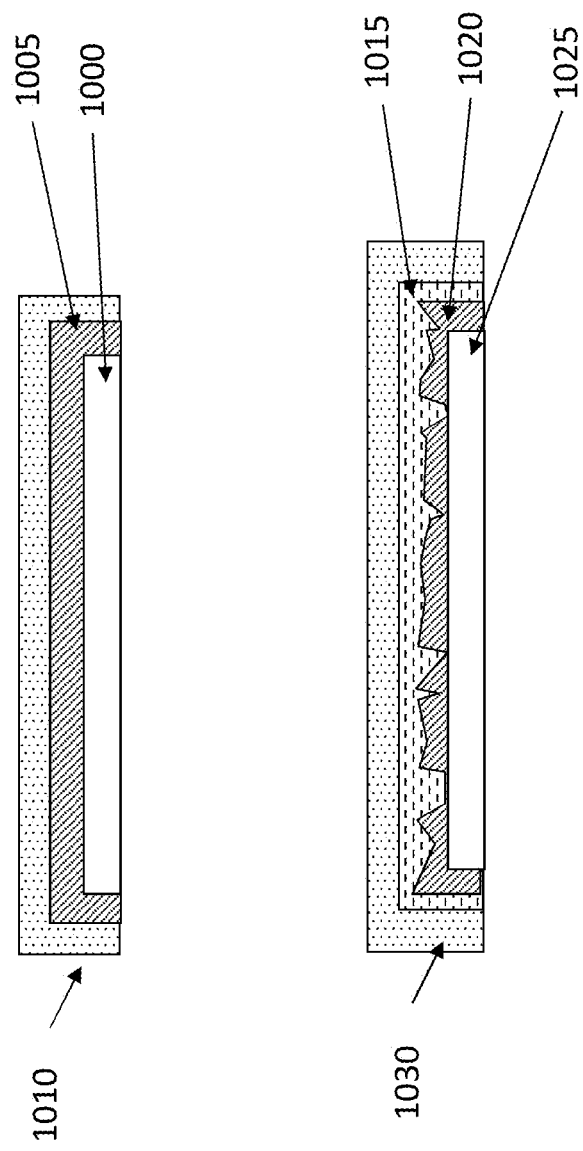

In some embodiments, it may be preferable to ensure that the top conductive porous layer is electrically disconnected from the bottom electrode layer. In fact, the top conductive porous layer itself can generate interfering currents from interfering compounds generated outside of the sensor. Additionally, the increased surface area can increase background currents. These interfering and background currents may be large enough in some scenarios to negate the benefit of increased surface area for collecting molecules from the enzyme sensing layer. There are multiple ways of maintaining electrical disconnection between the top porous layer and the bottom electrode layer. In FIG. 10, one way of maintaining the electrical separation is shown. The enzyme sensing layer (1005) is fabricated to have larger lateral dimensions than the bottom electrode layer (1000). The top porous layer (1010) is then fabricated to have larger lateral dimensions compared to the enzyme sensing layer, fully encapsulating the enzyme layer, while avoiding any electrical connection between the top and bottom layers.

In some embodiments, the enzyme-based sensing layer natively contains holes when deposited, causing the top and bottom layers to be electrically connected. In these cases, it may be necessary to deposit an additional insulator layer. For example, if an imperfect enzyme sensing layer (1020), containing holes, is deposited on the bottom electrode (1025), a thin, porous electrical insulator (1015) may be deposited on top of the enzyme sensing layer (1020), to separate the bottom electrode (1025) from the top, porous conductive electrode (1030). A variety of porous insulating materials may be used, including for example polyurethane and Nafion™ which are commonly used for this purpose in electrochemical sensors. In some cases, an inorganic insulator, such as silicon nitride or silicon dioxide, may be fabricated with pores to accomplish the same task. In general, the material for layer (1015) must be an electrical insulator and contain sufficiently large holes to readily allow the analyte of interest to reach the enzyme sensing layer. The thickness of this layer is determined by a number of factors, including the thickness required to maintain sufficient electrical insulation, porosity of the layer, nature of the deposition method of the top porous layer, and roughness and thickness of the underlying enzyme sensing layer. In general, this layer is made as thin as possible so that it does not impede the transport of analytes or other molecules to and from the sensing layer. For example, inorganic insulators which typically have superior insulation performance. If using an inorganic insulator, a layer between 10 nm to 500 nm may be sufficient to perform the function. If an organic insulator is used, a layer thickness of 100 nm to 5 micrometers may be used.

As known to the person of ordinary skill in the art, alternative methods for obtaining linear sensor performance require the use of organic control layers to control diffusion, for example polyurethane. The precise thickness of these layers, as well as their adhesion chemistry, are very dependent on the ambient humidity and temperature at which they are deposited. The variability, being hard to control, can introduce uncertainty in the measurements. The porous metal diffusion control layers described in the present disclosure offer a solution with improved ion collection efficiency and oxygen recycling, as none of the peroxide molecules are lost to the surrounding tissue, resulting in almost no reduction in measured sensor sensitivity. Therefore, using a porous metallic layer decreases the variability between different sensors, in turn increasing the accuracy and reliability of each sensor.

In addition to providing more linearity and oxygen insensitivity, the metal surface protective layers also enable the protection of enzyme molecules from attack, by hiding the sensing chemistry from the immune system, thereby yielding efficient electrochemical sensors with very thin enzyme layers that offer long lifetimes. The thickness of the enzyme layer determines the delay between the reaction of the sensor to the analyte molecules of interest, and the observation of the electrical signal from the released ions at the contact surfaces. This delay can be reduced, in the structures of the present disclosure, to be limited by the enzyme reaction speed determined by turn-over, rather than be limited by the diffusion rate of the ions within the polymer matrix.

Metal deposition through vacuum processing brings with it many potential pitfalls when thin and delicate organic materials are to be coated. However, by appropriate polymerization of the enzyme layer with glutaraldehyde and subsequent metallization using a platinum sputter deposition process, it is possible to deposit metallic layers on enzymes without much deterioration in their chemical performance. The metal/enzyme/metal sandwich layer can even be deposited onto a photoresist lift-off mask, and patterned by using a lithographic approach. This fabrication approach leaves the active sandwich layer only on top of the electrodes of interest, and thereby enables the functionalization of select areas with micrometer accuracy. The lift-off chemistry, which consists of using acetone to dissolve the photoresist stencil layer selectively, to define the pattern of metal/enzyme/metal functionalized areas, does not significantly reduce the enzyme activity of glucose oxidase, and permits sandwich structures to be defined on top of electrochemical potentiostat detectors. This may also hold true for other enzymes, such as lactate oxidase or urecase, and leads to the opportunity of defining several different chemical sensors on the same substrate by a series of lithographic processes depositing different enzyme layers onto electrochemical working electrodes. Therefore, in some embodiments, a sensor may comprise a plurality of areas, each area having a different enzyme layer, in order to detect a plurality of target analytes with the same sensor. Unlike sensor systems known in the art, in which peroxide or ammonia molecules can escape, metal-based multilayers as described in the present disclosure prevent escape of these molecules, avoid cross-talk and enable precise measurements of several analytes in close proximity.

In such traditional enzyme-based sensor systems, measuring more than one analyte within a compact sensor is typically very difficult, due to crosstalk. Specifically, many enzymes for different analytes generate the same reporter molecule (the reporter molecule being the molecule that generates sensing), and reporter molecules generated due to one analyte may be sensed by the electrode for another analyte. For example, an implantable sensor designed to measure both lactate and glucose may have two electrodes, one coated with lactate oxidase and one coated with glucose oxidase. When glucose levels are high, hydrogen peroxide generated by glucose oxidase may diffuse to the lactate oxidase electrode, falsely elevating the lactate reading. These electrodes may need to be separated, normally, by a distance of 1 mm or more to reduce crosstalk to acceptable levels, depending on the environment in which the sensor is implanted, and depending on the required accuracy. Wireless implantable sensors can be smaller than 1 mm, with electrodes as small as 200×200 microns, therefore this required separation can limit minimum device size when more than one analyte must be sensed. Because the metal/enzyme/metal sensor described in the present disclosure has a porous top layer designed to react with or capture any escaping hydrogen peroxide, or other reporter molecules, much less cross-talk occurs, and multi-analyte sensors can have separations of as little as 10-250 micrometers between working electrodes, depending on the required porosity of the top metal layer and depending on the required accuracy of each sensor. This advantage permits the fabrication of wireless implantable sensors with areas smaller than 1 $mm^2$, which can detect multiple analytes in one device.

Figure 3:
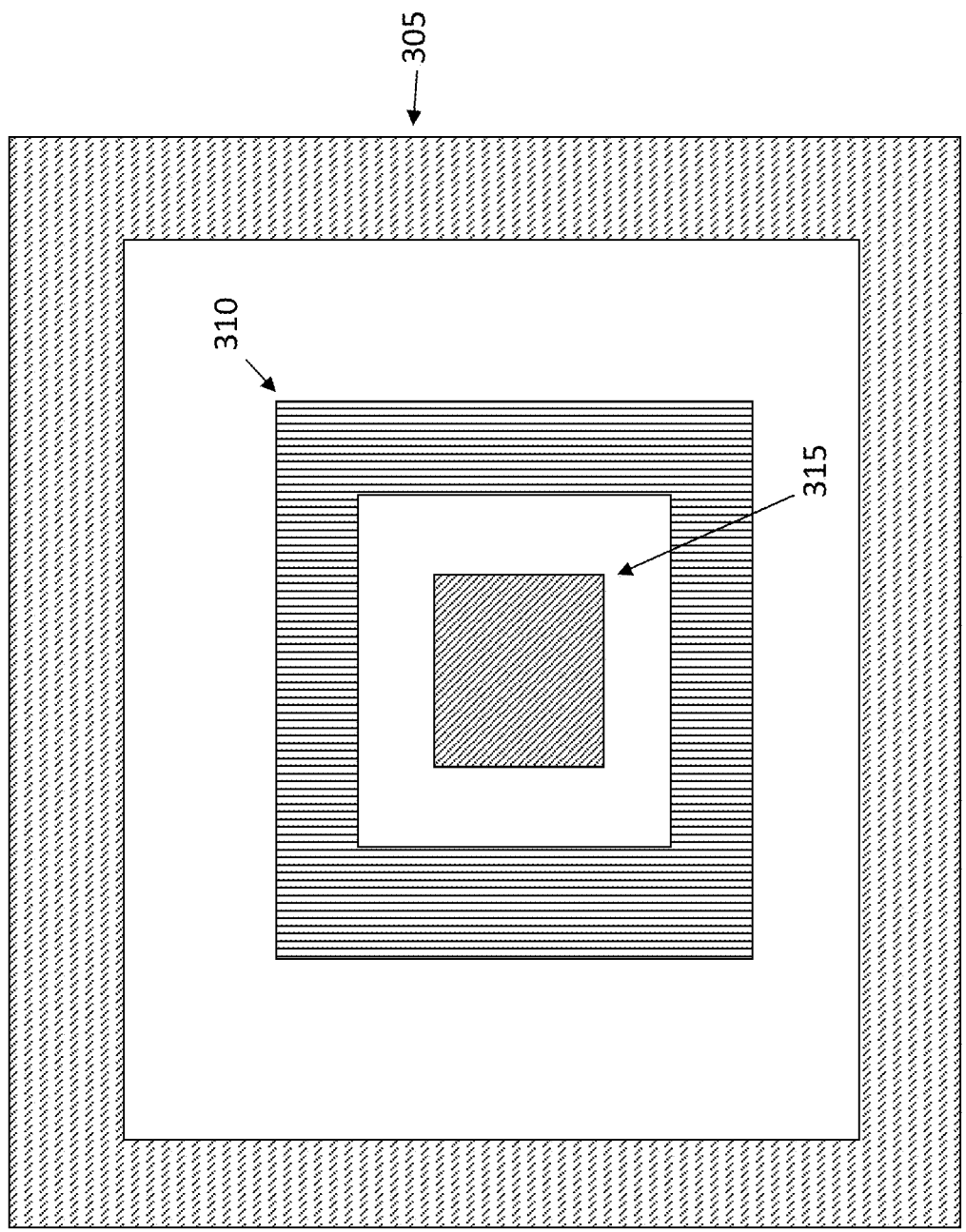
FIG. 3 illustrates an exemplary electrode configuration.

In some embodiments, the sensor can also comprise wireless electronics to transmit its measurements from within a human body to external equipment. The sensor, for example, may have dimensions of 1.2 mm by 1.2 mm, a fast response time of 0.1 s, use a low power of 5 microWatts, and cost only 10 cents. Sensors with millimeter scales dimensions do not move with respect to surround cells, maintaining a constant impedance. The sensors can also be implanted in many locations due to their small size, they can be injected, and produce small tissue irritation. Possible applications comprise monitoring of chronic diseases such as diabetes, kidney failure, cardiovascular problems and cancer. The sensors can also be used in skin patches to monitor cortisol, alcohol, glucose, and applications such as sport medicine and post-operative monitoring. Power can be transmitted to the sensor through wireless transmission, for example using coil antennas. A typical configuration for the electrode may be used, for example with concentric, square, working, reference and counter electrodes. For example, FIG. 3 illustrates a configuration with a counter electrode (305), a reference electrode (310), and a working electrode (315).

Figure 4:
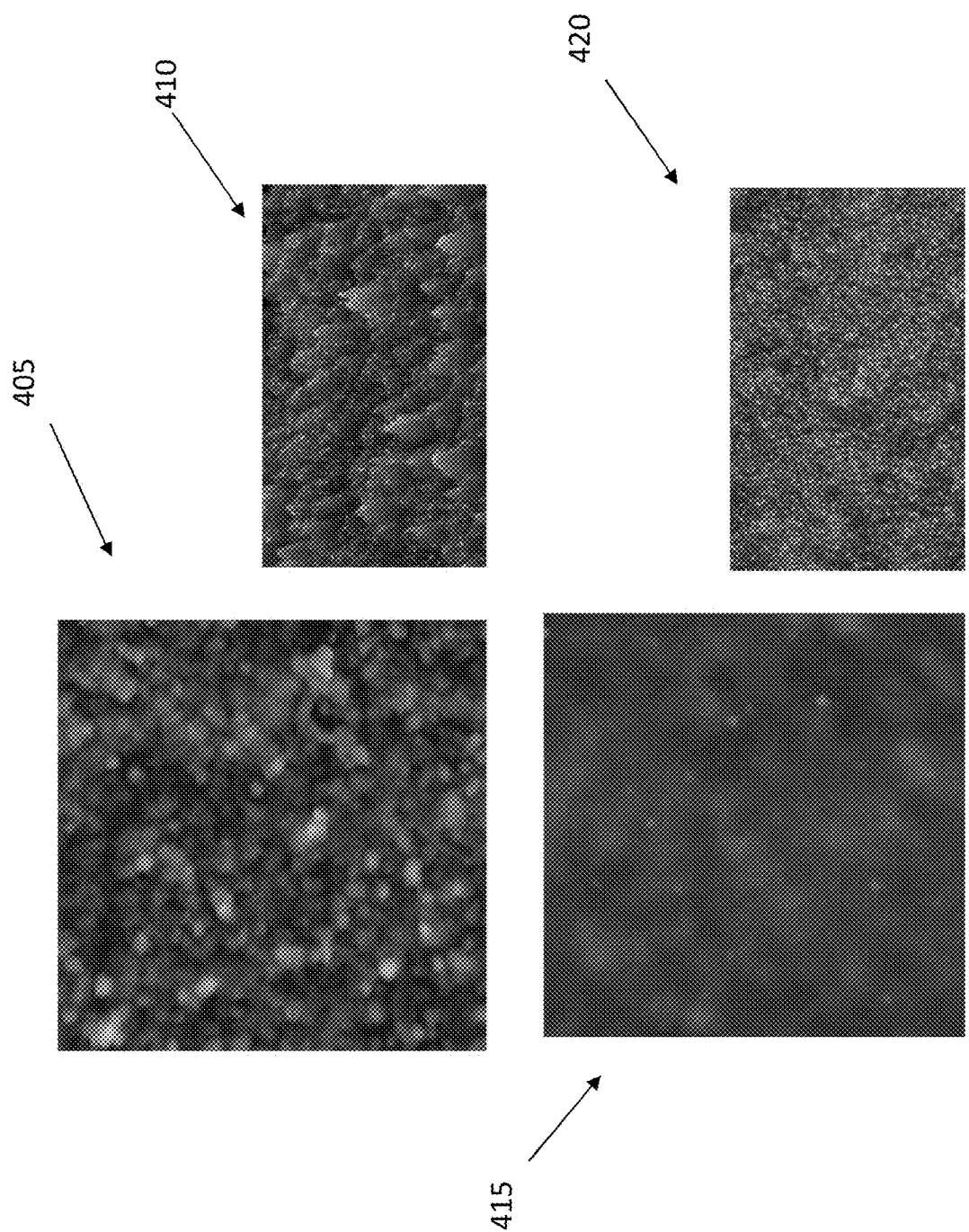
FIG. 4 illustrates exemplary images of irregular peaks.
Figure 5:
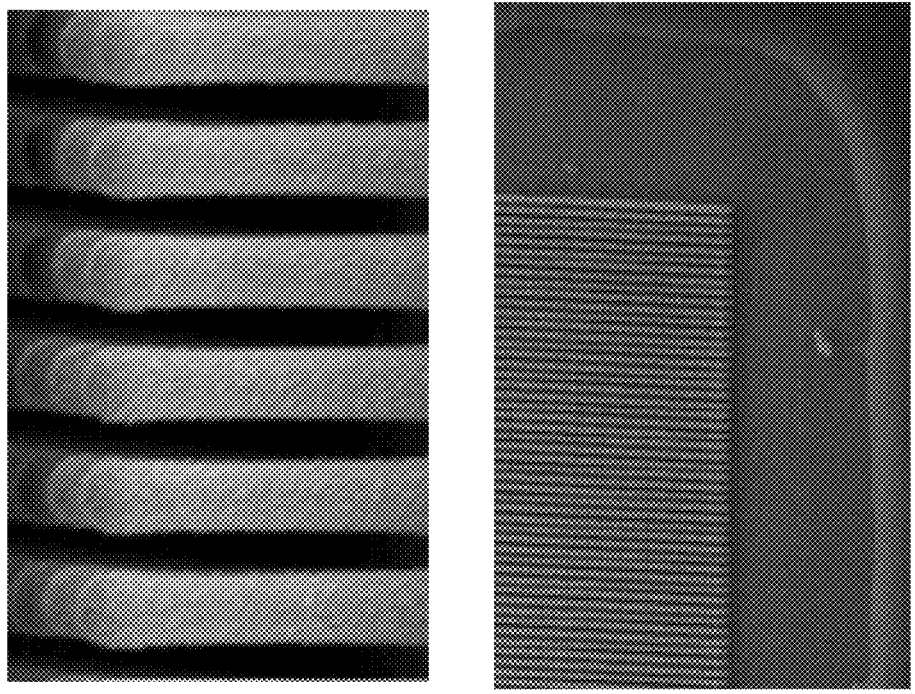
FIG. 5 illustrates exemplary periodic nanopillars.

In some embodiments, platinum is used to fabricate all three electrodes. Platinum allows the use of lower voltages and a more stable operation compared to known Ag/AgCl electrodes. FIG. 4 illustrates atomic force microscope images of an exemplary electrode structure with higher irregular peaks for use in high current sensors, e.g. 500 nA: (405,410). FIG. 4 also illustrates lower peaks for use in low current sensors, e.g. 5 nA: (415,420). FIG. 5 illustrates exemplary nanopillars that can be fabricated on the surface of an electrode to increase its surface area and sensitivity. The nanopillars are shown in a close-up in the top picture of FIG. 5 and in a top perspective view in the bottom picture of FIG. 5. The nanopillars can be of the same metallic material to form a uniform electrode. In some embodiments, the sensors are fabricated by spin coating the enzyme, instead of drop coating. Spin coating allows thinner electrode layers. As hydrogen peroxide must diffuse to the metal electrode surface to be measured, thinner enzyme layers increase the collection efficiency of the sensor. In some embodiments, the enzyme hydrogel layers are no thicker than 1 micrometer, and generally between 2 nm and 1 micrometer. Enzyme molecules are typically larger than 1-2 nanometers, therefore the minimum enzyme layer is typically the size of the enzyme molecule. The top electrode controls the rate of transfer for the target analyte to diffuse through the pores in the metal, towards the enzyme layer, and the rate of transfer of the peroxide. The top metallic layer can have pores (or pinholes) between 1 nm and 1 micrometer. The metallic layer forms an electrochemical capacitor, therefore its porous structure affects the electrical properties of the sensor. The bottom metallic layer can be as thick as necessary since it provides structural support for the other layers.

In some embodiments, platinum provides the best choice for the porous layer, as it matches the working electrode and reference electrode materials, it is inert, and lasts for a long time. In some embodiments, gold can be used as it not very reactive, and can be generally considered biocompatible. Gold can complicate the measurements within the electronic cell as there may be galvanic voltages and currents between gold and the reference electrode. Tungsten can also be used, as it is inert and generally biocompatible, but can also complicate measurements with galvanic interactions. Titanium is a biocompatible material, therefore it can also be used, though it tends to oxidize, but the oxide is conductive so oxidization is not generally a problem, though electrochemical interaction can be problematic. Palladium is a material used in many implants and can be considered reasonably biocompatible. Iridium is biocompatible but very expensive. Silicon has some conductivity and it is reasonably biocompatible, however it can generate galvanic interactions. In some embodiments, the above metals or other metals can be used, as well as their alloys. Semiconductors may also be used, as well as conductive metallic oxides such as, for example, $TiO_2$, $WO_3$, $SnO_2$, $InO_2$, etc. Deposition techniques used may be vacuum techniques, such as sputter deposition and vapor deposition, as well as electroplating or electro-less plating.

The pores in the metallic, protective structures are large enough for glucose, oxygen, and water to go through, but small enough to avoid cells and large molecules from attacking the enzyme. Therefore, the pore size or diameter can, in some embodiments, range from 2 nanometers to 2 micrometers. In some embodiments, the pore size is below 200 nanometers, or below 20 nm. Controlling the porosity of the layer enables controlling the amount of oxygen that can escape from the enzyme layer, and the amount of glucose that can enter the enzyme layer. It is possible to define a porosity ratio for the sensor by considering the area of the pores as the open area of the sensor which allows passage of chemical species, and comparing it to the closed area of metal around the pores. The porosity ratio can be, in some embodiments, between 0.001% and 50%. In some embodiments, the porosity ratio is between 0.1% and 10%, and can be controlled by controlling the deposition parameters. In other words, the open area of the pores is between 0.001% and 50% of the total area of the porous layer, or between 0.1% and 10% of the total area of the porous layer.

In some embodiments, the layer thicknesses of the three individual layers of the sandwich structure are as in the following. The bottom (contact) layer can be between 1 nm and 1 mm thick, as it needs to provide a conducting substrate. Needles could be used, or metallic layers could be deposited onto silicon chips or polymer supports. The top (protective) layer can be between 1 nm and 10 micrometer thick. In some embodiments, the top metallic layer is thinner than 1 micrometer, or thinner than 100 nm. In some embodiments, the enzyme layer can be between 10 nm and 50 micrometers. In some embodiments, the enzyme layer has a thickness below 10 micrometers, or less than 1 micrometer, or less than 400 nm.

Figure 2:
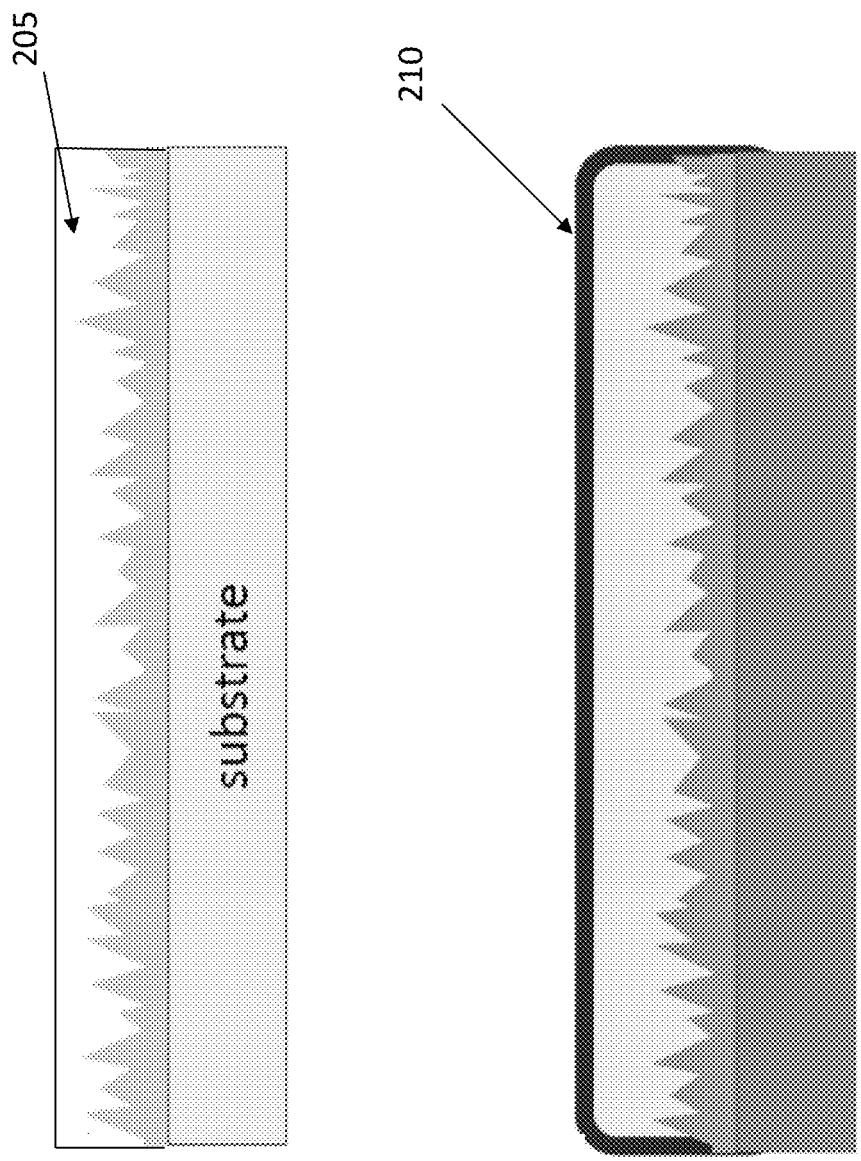

FIG. 1 illustrates a substrate (105) and a metallic layer (110) for a working electrode, for example made of Pt by sputter deposition. The metallic layer is patterned to produce a higher surface area (115). The pattern may be irregular pillars such as in FIG. 1, or regular, periodic pillars as in FIG. 5. As illustrated in FIG. 2, an enzyme layer (205) is spin coated onto the patterned metallic layer. For example, an enzyme hydrogel can be used. For example, an enzyme and BSA coating can be used. A layer of glutaraldehyde (210) can be deposited to crosslink the enzyme hydrogel, for example by vacuum evaporation. For example, glutaraldehyde in a water solution within an open container is inserted in a vacuum chamber, leading to evaporation onto the sample within the chamber. In some embodiments, this process is applied on the working electrode only, while in other embodiments it can also be applied to one or two of the other electrodes of FIG. 3. In some embodiments, layer (210) in FIG. 2 may comprise a bottom layer of glutaraldehyde and a porous metallic layer on top of the glutaraldehyde. In some embodiments, layer (210) does not comprise glutaraldehyde but only a porous metallic layer.

Figure 6:
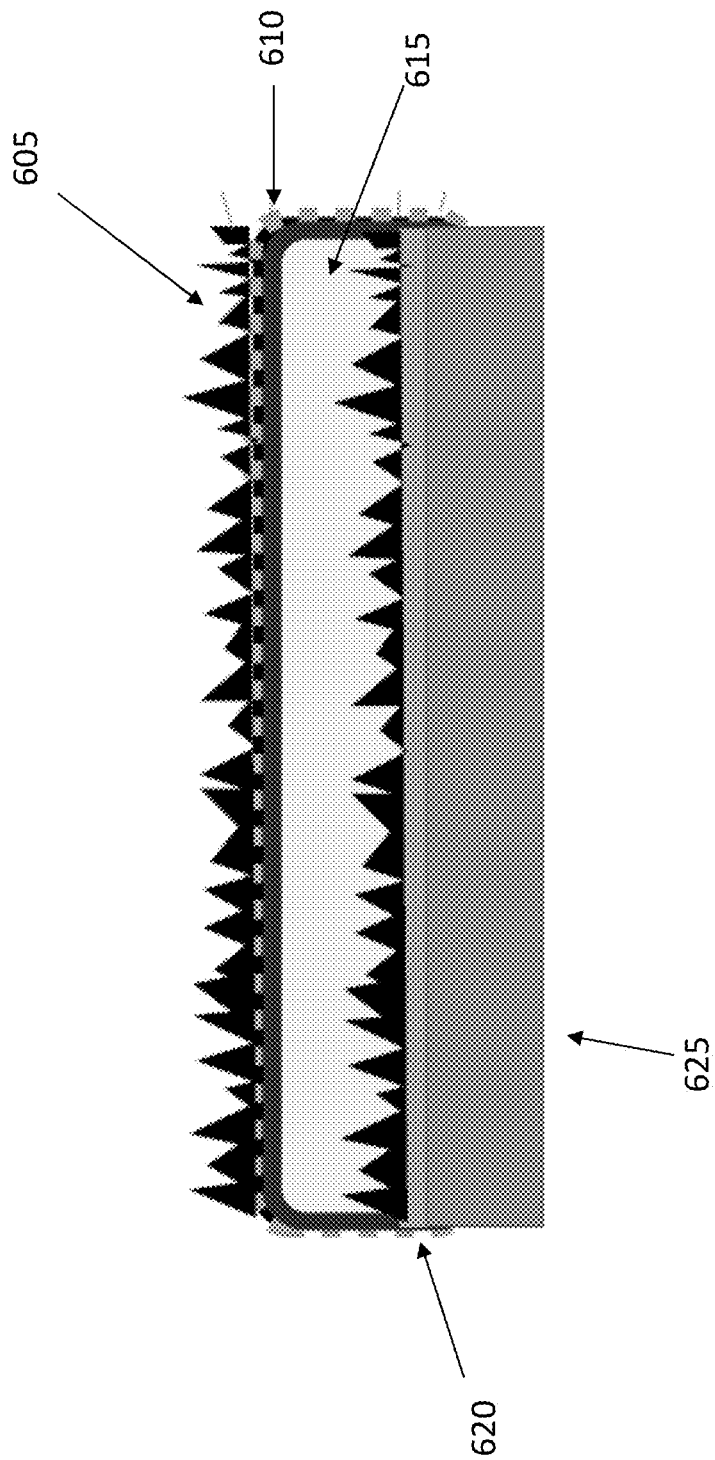
FIG. 6 illustrates an exemplary sensor with a protective metallic top layer.

FIG. 6 illustrates an exemplary sensor with a protective metallic top layer. The sensor comprises a substrate (625), a first metallic, patterned layer (620), an enzyme hydrogel layer (615), and a second, metallic patterned layer to protect the enzyme hydrogel. The second layer comprises a porous layer (610), which has openings allow passage of select chemical species while blocking other chemical species. The second layer can also have a patterned area on top (605). For example, the top porous Pt layer may be 50 nm thick, the enzyme layer may be 300 nm thick, and the Pt bottom layer may be 100 nm thick.

Figure 7:
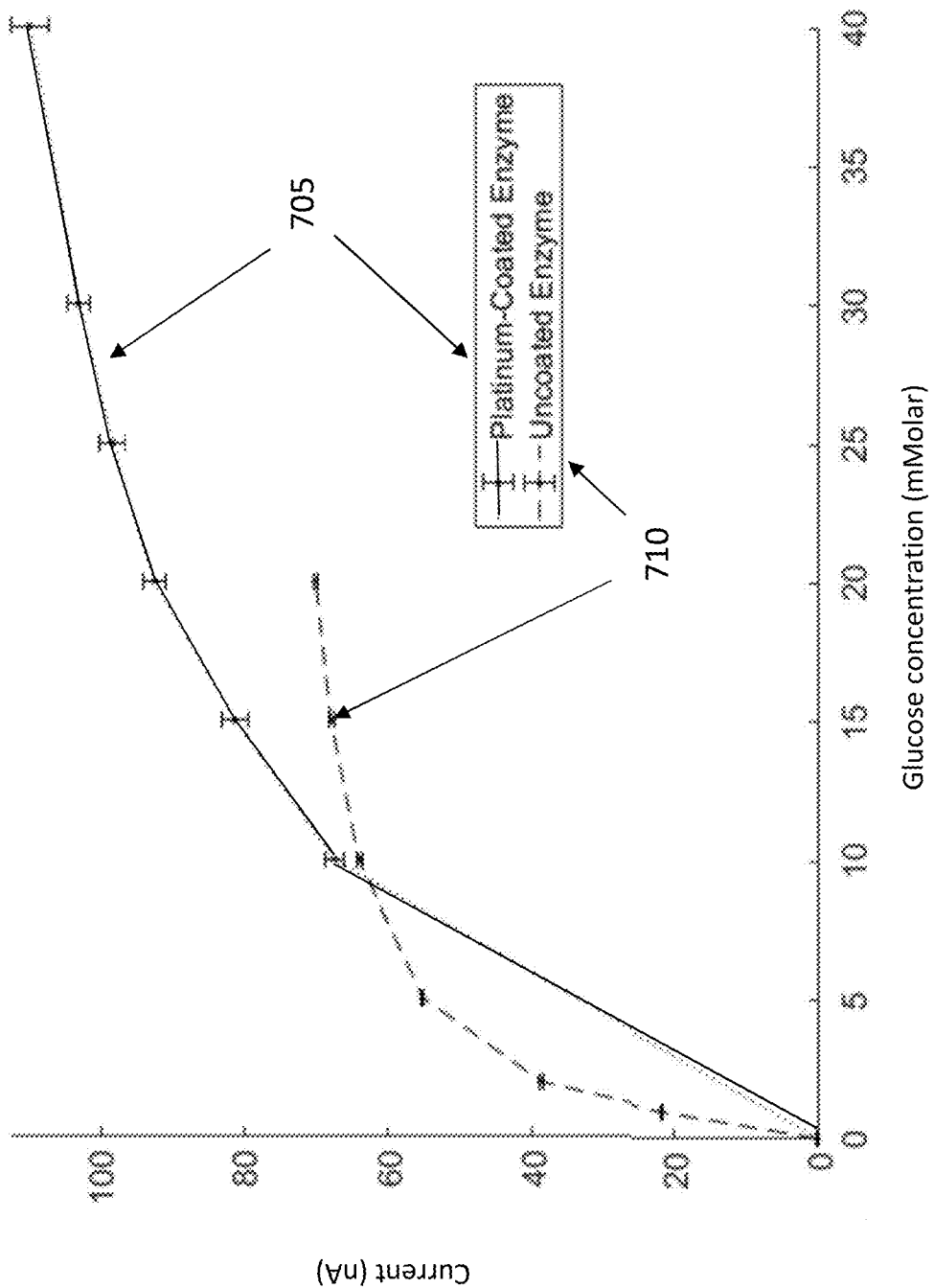
FIG. 7 illustrates exemplary data.

FIG. 7 illustrates exemplary data comparing a sensor with an uncoated enzyme layer (710), with the superior performance of a sensor having a protective porous layer as described in the present disclosure (705). In some embodiments, the sensor can comprise enzymes such as glucose oxidase, lactate oxidase, xanthine oxidase, cholesterol oxidase, sarcosine oxidase, cortisole oxidase, urate oxidase, alcohol oxidase, glutathione oxidase, and nicotine oxidase. In some embodiments, the sensor can be attached to the skin with an adhesive patch, for example to monitor sweat or iontophoretically extracted materials. The external sensor may be part of a fitness tracker with an external battery and communication modules.

Figure 8:
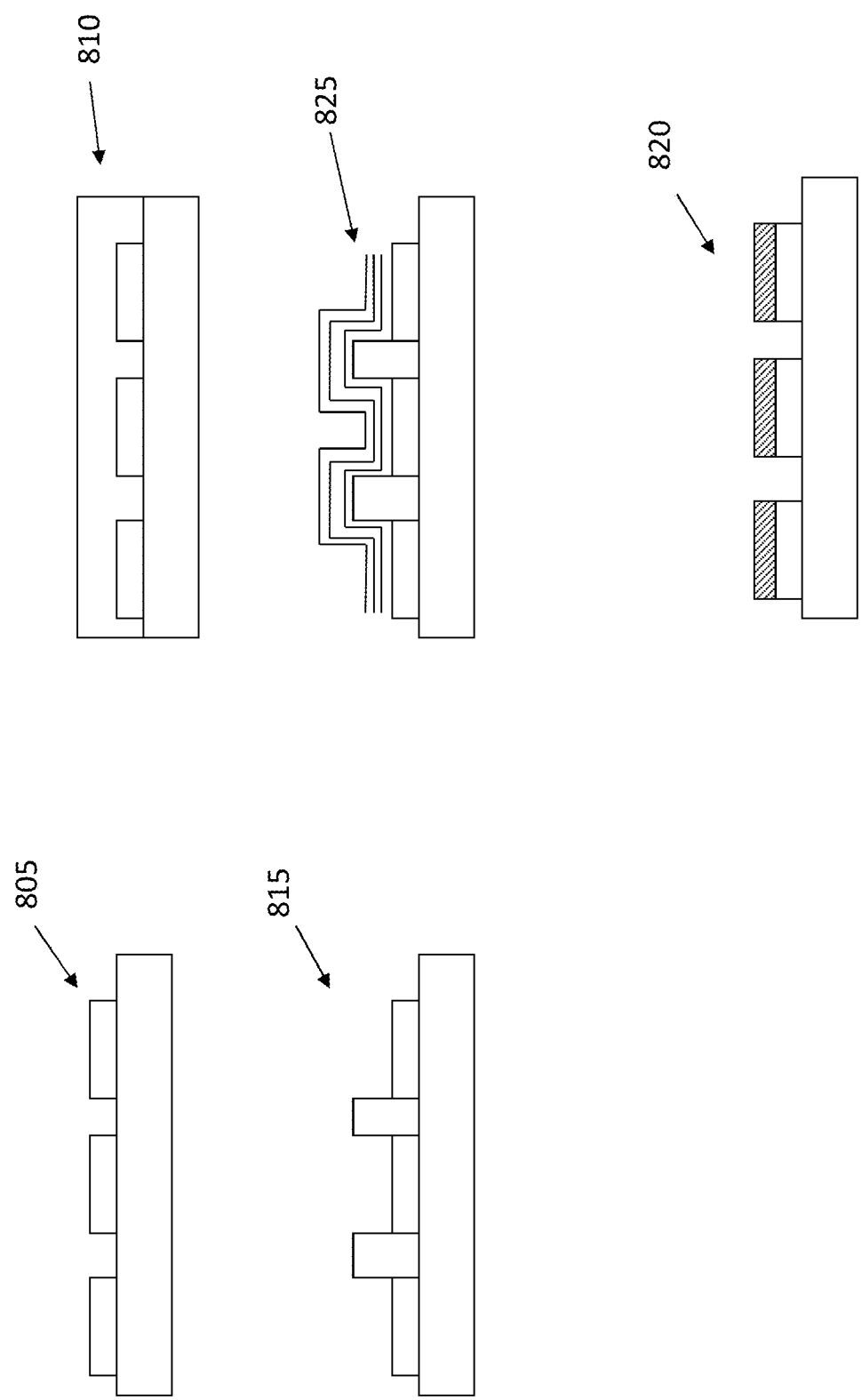
FIG. 8 illustrates a schematic approach of building an electrochemical sensor on a flat substrate.

FIG. 8 illustrates an exemplary photolithography process: a sensor comprises three electrodes (805); a photoresist is spin coated on the sensor (810); after exposition to light, part of the photoresist is lifted off (815), allowing the deposition of multiple layers, such as the enzyme and crosslinker, and the porous metallic protective layer; the remaining photoresist is completely lifted off (820), and the three sensors now have an enzyme hydrogel and porous metallic layer on top. For example, as visible in FIG. 8 (825), three layers can be deposited on the resist, comprising a first metallic layer, an enzyme layer, and a porous metallic layer on top. In some embodiments, where the sensing device is fabricated by lithographic processes, it is possible to use the metal deposited on top of the enzyme layer to protect the underlying enzyme molecules during lithographic processing (i.e. exposure to acetone, etc.).

The present disclosure describes a structure, consisting of a layer of reactive material on a substrate, covered with a porous inorganic layer capable of controlling the flow of reagents and/or products into or out of the reactive material to control reaction rates. In some embodiments, the inorganic porous layer is platinum, gold, tungsten, iridium, titanium, carbon (including graphene or carbon nanotubes) or an otherwise biocompatible material with very low immunogenicity, and the reactive layer is enzymatic. In some embodiments, the inorganic layer is platinum or another catalytic metal capable of reducing reactive oxygen or oxidation species before they can reach the sensitive reactive layer. In some embodiments, the sensor is capable of quantifying a specific analyte, the reactive layer is an enzyme in the oxidase family, and the porosity of the inorganic layer is controlled such that oxygen can freely enter the reaction layer, the analyte is restricted, and other interfering or damaging species (including immune cells) are rejected, improving the overall sensitivity, oxygen independence and high analyte concentration performance of the system.

In some embodiments, the sensor is part of a power generation cell, the reactive layer is an enzyme, and interfering or damaging species (including immune cells) are rejected from the compartment. In some embodiments, the sensor comprises a layer of reactive material on a substrate, covered with a porous conductive layer capable of controlling the flow of reactants and/or products into or out of the reactive material and electrochemically transducing chemical species within the reaction chamber into or out of external circuitry, thereby improving the transduction efficiency of that chemical species. In some embodiments, the substrate is itself conductive, and periodic or occasional electrically conductive attachments are made between the porous conductive layer and the substrate, thereby greatly improving the transduction efficiency of the chemical species of interest. In some embodiments, the substrate and porous conductive layer individually are composed of platinum, PEDOT:PSS, or other biocompatible conductive material capable of electrochemical transduction, the conductive attachments are composed of a biocompatible conductive material, and the reactive layer is enzymatic.

In some embodiments, the sensor is capable of quantifying a specific analyte, and the porosity of the inorganic layer is controlled so that the analyte and reactants can freely enter the reaction layer and other interfering or damaging species (including immune cells) are rejected, thereby permitting electrochemically active products to be transduced with very low loss due to the near complete encapsulation of the reactive layer. In some embodiments, the sensor is part of a power generation cell, and the porosity of the inorganic layer is controlled such that the reactants can freely enter the reaction layer and other interfering or damaging species (including immune cells) are rejected, thereby permitting electrochemically active products to produce energy with very low loss due to the near complete encapsulation of the reactive layer. In some embodiments, the biosensor comprises a reactive layer based on an oxidase enzyme. In some embodiments, the pores are sized to promote the flow of oxygen into the reactive layer, reject the entrance of interfering and damaging species, including immune cells, into the reactive layer, reduce the loss of hydrogen peroxide from the reactive layer, and optionally reduce the flow of analyte into the reactive layer with respect to oxygen to improve the linearity of the biosensor at high analyte concentrations.

In some embodiments, the porous layer and substrate are composed of platinum, which has nearly no immunogenicity, and is capable of catalytically reducing damaging reactive oxygen species. In some embodiments, the nearly complete encapsulation of the reactive layer permits nearly all hydrogen peroxide generated by the reactive layer to be captured, and much of the oxygen generated by the oxidation of hydrogen peroxide is reused by the reactive layer, improving the sensitivity and linearity of the biosensor.

In some embodiments, the porous, conductive electrode is partially covered and filled with a reactive material, such that the transduction of desirable reaction products is maximized, and regeneration of reactants for the reactive material by the conductive electrode is maximized. In some embodiments, the conductive electrode is part of a sensor and composed of platinum, the reactive material contains an oxidase enzyme, the desirable reaction product is the analyte of interest, the regenerated reactant is oxygen, thereby improving the linearity of the sensor is improved at high analyte concentrations, and the overall sensitivity is improved. In some embodiments, the electrode is part of an energy harvesting system.

In some embodiments, the enzyme layer is deposited by dipping, inkjet printing, spin coating and the top protecting metal is deposited by a vacuum deposition technique to deliberately contain pinholes or other microfabricated conduits for products and reagents to travel through the metal membrane. In some embodiments the metallic layers of the electrodes comprise irregular jagged peaks, or an array of nanopillars. In some embodiments, the device can be implanted internally. In some embodiments, the three electrodes have concentric square shapes as in FIG. 3.

In some embodiments, the sensing device can comprise only two electrodes instead of three electrodes. In these embodiments, the two electrodes each comprise a multilayer as described in the present disclosure, comprising a protective, porous metallic layer. In other embodiments, the sensing device may comprise a single electrode instead of three or two electrodes. For example, one electrode systems use the body of the organism that is being measured as ground, and the single working electrode to take measurements.

In some embodiments, the top porous layer is not necessarily metallic but may be conductive as to improve the collection of any electroactive species, and may have catalytic activity towards any damaging chemical species (such as reactive oxygen species generated by the immune system). For example, this top porous conductive layer may be composed of PEDOT:PSS or a polypyrrole. As explained with reference to FIG. 10, in some embodiments the metallic porous layer is electrically disconnected from the metallic layer.

In some embodiments, the porosity of the top layer is intrinsic to the deposition method. For example, adjusting deposition parameters during e-beam evaporation or sputtering of metal films can be used to control porosity. In some embodiments, the porosity of the top layer may be more deliberately patterned. For example, the exact positions and sizes of the pores may be selected using e-beam lithography or photolithography. For example, a mask containing a pattern of holes may be deposited on top of a non-porous top layer, and subsequently used to etch controlled holes into the top layer. In this way, the porosity of the top layer may be better controlled than may be possible when the film is natively deposited with pores.

Figure 11:
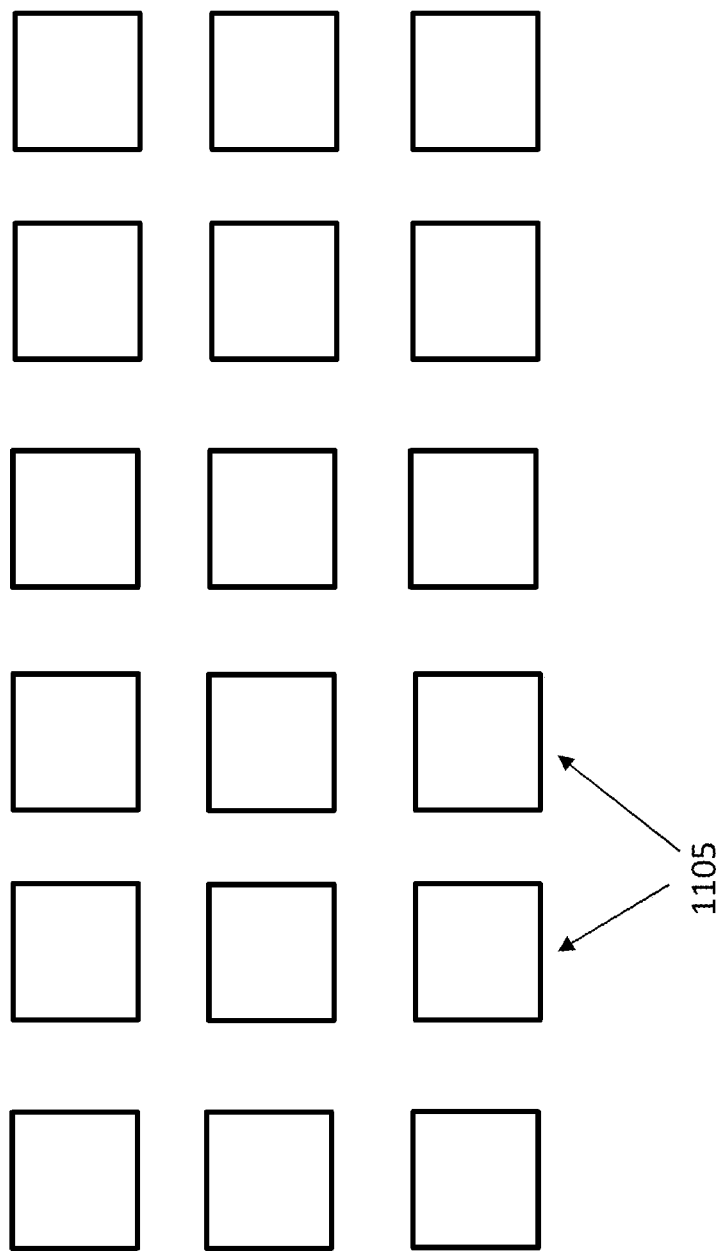
FIG. 11 illustrates an exemplary array of sensing devices.

In some embodiments, the bottom sensing layer is not necessarily a metal, but a conductive electrode material. For example, carbon, polypyrroles, and PEDOT have commonly been used as non-metallic electrode materials. In some embodiments, the sensing devices can be arranged in an array. A biosensor can therefore comprise an array of sensing devices as described in the present disclosure, wherein a spacing between the sensing devices of the array of sensing devices is configured to avoid crosstalk due to leakage of intermediate reporting molecules produced during the sensing process. FIG. 11 illustrates an exemplary array of sensing devices, where each device (1105) is as described above in the present disclosure.

The examples set forth above are provided to those of ordinary skill in the art as a complete disclosure and description of how to make and use the embodiments of the disclosure, and are not intended to limit the scope of what the inventor/inventors regard as their disclosure.

Modifications of the above-described modes for carrying out the methods and systems herein disclosed that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

It is to be understood that the disclosure is not limited to particular methods or systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

What is claimed is:

1. A sensing device comprising:
a working electrode on a substrate;
wherein:
the working electrode comprises:
a metallic layer contacting the substrate;
an enzyme layer on the metallic layer; and
a metallic porous layer on the enzyme layer,
the metallic layer, the enzyme layer, and the metallic porous layer are configured to detect a target analyte through an electrochemical reaction, and
the metallic porous layer is electrically connected to the metallic layer.

2. The sensing device of claim 1, wherein the metallic layer comprises an array of pillars.

3. The sensing device of claim 2, wherein the enzyme layer is deposited between the pillars.

4. The sensing device of claim 1, wherein the metallic porous layer comprises an array of pores having a diameter between 2 nm and 2 micrometers.

5. The sensing device of claim 4, wherein the array of pores has a total area between 0.001% and 50% of a total area of the metallic porous layer.

6. The sensing device of claim 5, wherein the metallic porous layer is made of a material selected from the group consisting of: Pt, Au, W, Ti, Pd, Ir, Si, $TiO_2$, $WO_3$, $SnO_2$, graphene, and $InO_2$.

7. The sensing device of claim 6, wherein the enzyme layer comprises an oxidase enzyme and a hydrogel.

8. The sensing device of claim 7, wherein the enzyme layer comprises an oxidase enzyme selected from the group consisting of: glucose oxidase, lactate oxidase, xanthine oxidase, cholesterol oxidase, sarcosine oxidase, cortisol oxidase, urate oxidase, alcohol oxidase, glutathione oxidase, and nicotine oxidase.

9. The sensing device of claim 8, wherein the sensing device is configured to be implanted internally to an organism, or configured to be attached externally to skin of the organism.

10. The sensing device of claim 7, wherein the enzyme layer further comprises glutaraldehyde.

11. The sensing device of claim 4, wherein the array of pores has a total area between 0.1% and 10% of a total area of the metallic porous layer.

12. The sensing device of claim 4, wherein the metallic porous layer comprises an array of pores having a diameter between 2 nm and 200 nm.

13. The sensing device of claim 12, wherein the metallic porous layer comprises an array of pores having a diameter between 2 nm and 20 nm.

14. The sensing device of claim 1, wherein the metallic layer has a thickness between 1 nm and 1 mm.

15. The sensing device of claim 14, wherein the metallic porous layer has a thickness between 1 nm and 10 micrometers.

16. The sensing device of claim 15, wherein the enzyme layer has a thickness less than 10 micrometers.

17. The sensing device of claim 16, wherein the enzyme layer has a thickness less than 1 micrometer.

18. The sensing device of claim 15, wherein the enzyme layer has a thickness less than 400 nm.

19. The sensing device of claim 1, further comprising:
a counter electrode on the substrate; and
a reference electrode on the substrate,
wherein:
the counter electrode comprises:
a metallic layer contacting the substrate;
an enzyme layer on the metallic layer of the counter electrode; and
a metallic porous layer on the enzyme layer of the counter electrode, and
the reference electrode comprises:
a metallic layer contacting the substrate;
an enzyme layer on the metallic layer of the reference electrode; and
a metallic porous layer on the enzyme layer of the reference electrode.

20. The sensing device of claim 19, wherein the working electrode, the counter electrode, and the reference electrode have concentric square shapes.

21. The sensing device of claim 1, wherein the target analyte is glucose, and the enzyme layer comprises glucose oxidase.

22. The sensing device of claim 1, wherein:
the enzyme layer comprises a plurality of holes, and
the holes are filled with the metallic porous layer, thereby forming the electrical connection between the metallic porous layer and the metallic layer.

23. The sensing device of claim 1, wherein:
the enzyme layer is laterally smaller than the metallic layer, and
the metallic porous layer surrounds lateral sides of the enzyme layer, thereby forming the electrical connection between the metallic porous layer and the metallic layer.

24. The sensing device of claim 1, wherein:
the metallic layer comprises pillars, and
spaces between the pillars are filled with the enzyme layer, thereby forming the electrical connection between the metallic porous layer and top surfaces of the pillars of the metallic layer.

25. An array of sensing devices according to claim 1, wherein a spacing between the sensing devices of the array of sensing devices is configured to avoid crosstalk due to leakage of intermediate reporting molecules.

26. The array of claim 25, wherein the spacing is between 10 nm and 250 nm.

* * * * *